US00RE36857E

United States Patent [19]

Euteneuer et al.

[11] E Patent Number: Re. 36,857

[45] Reissued Date of Patent: Sep. 5, 2000

[54] INTERLOCKING PEEL-AWAY DILATION CATHETER

[75] Inventors: Charles L. Euteneuer, St. Michael; Daniel O. Adams, Blaine, both of Minn.

[73] Assignee: SciMed Life Systems, Inc., Maple Grove, Minn.

[21] Appl. No.: 08/355,141

[22] Filed: Dec. 13, 1994

Related U.S. Patent Documents

Reissue of:

[64] Patent No.: 5,171,222
Issued: Dec. 15, 1992
Appl. No.: 07/554,182
Filed: Jul. 18, 1990

U.S. Applications:

[63] Continuation of application No. 07/166,976, Mar. 10, 1988, abandoned.

[51] Int. Cl.[7] ..... A61M 29/00; A61M 5/178

[52] U.S. Cl. ..... 604/102; 604/160; 606/194

[58] Field of Search ..... 604/96–102, 160, 604/161; 606/192, 194, 198

[56] References Cited

U.S. PATENT DOCUMENTS 3,262,449 7/1966 Pannier, Jr. et al. .
3,297,030 1/1967 Czorny et al. .
3,550,591 12/1970 MacGregor .
3,559,643 2/1971 Pannier, Jr. et al. .
4,345,596 8/1982 Young .
4,412,832 11/1983 Kling et al. .
4,581,025 4/1986 Timmermans .
4,631,059 12/1986 Wolvek et al. .
4,687,469 8/1987 Osypka .
4,747,833 5/1988 Kousai et al. .
4,748,982 6/1988 Horzewski et al. .
4,771,777 9/1988 Horzewski et al. .
4,801,294 1/1989 Okada .
4,887,997 12/1989 Okada .
4,988,356 1/1991 Crittenden et al. .

FOREIGN PATENT DOCUMENTS 0 282 143 A1 9/1988 European Pat. Off. .

*Primary Examiner*—Corrine M. McDermott
*Attorney, Agent, or Firm*—Crompton, Seager & Tufte LLC.

[57] ABSTRACT

A dilatation balloon catheter which is capable of being removed from a patient while leaving a guide wire in place has a longitudinal slit extending from its proximal end to a position near its inflatable balloon. The catheter has an inflation lumen for applying fluid to inflate the balloon, and an insertion lumen through which the guide wire passes. The slit communicates with the insertion lumen so that the catheter can be peeled off of the guide wire as the catheter is withdrawn from the patient and the guide wire remains in place in the patient.

36 Claims, 4 Drawing Sheets

D
2
10
12
14
16
18
20
22
24
26
28
30
32
34
36
38
40
42
44
46
48
50
52

INTERLOCKING PEEL-AWAY DILATION CATHETER

Matter enclosed in heavy brackets [ ] appears in the original patent but forms no part of this reissue specification; matter printed in italics indicates the additions made by reissue.

This is a continuation of application Ser. No. 166,976 filed on Mar. 10, 1988, abandoned as of the date of this application.

BACKGROUND OF THE INVENTION

1. Field of the Invention.

The present invention relates to the field of angioplasty. In particular, the present invention relates to dilatation balloon catheters which are insertable into a patient over a guide wire.

2. Description of the Prior Art.

Angioplasty has gained wide acceptance in recent years as an efficient and effective method for treating certain types of vascular diseases. In particular, angioplasty is widely used for opening of stenosis in the coronary arteries, although it is also used for treatment of stenoses in other parts of the vascular system.

The most widely used form of angioplasty makes use of a balloon catheter which has an inflatable balloon at its distal end. Using fluoroscopy, the physician guides the catheter through the vascular system until the balloon is positioned across the stenosis. The balloon is then inflated by supplying fluid under pressure through an inflation lumen to the balloon. The inflation of the balloon causes stretching of the artery and pressing of the lesion into the artery wall to reestablish acceptable blood flow through the artery.

Guide wires are often used for establishing the path to the stenoses so that the balloon catheter can subsequently be positioned. The guide wire normally is advanced through the stenosis, and commonly is left in place during the inflation of the balloon.

Balloon catheters used for angioplasty are available in different balloon diameters. There are instances in which it becomes necessary to exchange one size of balloon catheter for another during an angioplasty procedure. When this happens, it is very advantageous to leave the guide wire in place while the first balloon catheter is removed. This allows the second balloon catheter to be reinserted without having to first reestablish the path by inserting a new guide wire.

In the past, however, the removal of the balloon catheter without removing the guide wire has been complicated because the balloon catheter is inserted over the guide wire. To remove the balloon catheter, while leaving the guide wire in place, there must be a portion of the guide wire extending out of the balloon catheter at the proximal end so that the guide wire can be gripped and held in place as the balloon catheter is removed.

One solution is to remove the initial guide wire while leaving the catheter in place and then inserting an "exchange wire" in its place. The exchange wire is long enough so that the portion of its length extending outside of the patient is longer than the length of the catheter. This allows a portion of the exchange wire to be available for gripping at all times regardless of the position of the catheter. There are, however, several problems with this approach. The use of an exchange wire essentially doubles the normal length of the guide wire, which makes the exchange wire difficult to handle and manipulate. This extra length is normally of no use to the physician during angioplasty, since exchanging catheters is required only in a fraction of the total number of angioplasty procedures. The extra steps of exchanging the guide wire for an exchange wire and the increased difficulty of handling a wire of much greater length have been required in the past in order to exchange balloon catheters. A more convenient and easier to use system would be desirable.

SUMMARY OF THE INVENTION

The present invention is a balloon catheter which can be removed from a patient over a standard length guide wire (typically about 150 cm) without removing the guide wire from the patient. The catheter of the present invention includes means for opening a longitudinal slit which communicates with the insertion lumen through which the guide wire passes. The slit extends from near the proximal end of the catheter to a position near the inflatable balloon, so that the length of the catheter which does not contain a slit is shorter than the length of guide wire normally located outside of the patient and extending beyond the proximal end of the catheter.

To remove the catheter from the patient, the guide wire is held in place while the catheter is removed from the patient. The guide wire exits the catheter through the slit, so that as the catheter is withdrawn from the patient, the distance between the exit of the guide wire from the catheter and the distal end of the catheter becomes progressively shorter. In other words, the catheter tube is "peeled away" from the guide wire as the catheter is withdrawn from the patient. When the catheter has reached a position in which the distal end of the catheter is outside of the patient and the guide wire can be grasped beyond the distal end of the catheter, the remainder of the catheter can be pulled off of the proximal end of the guide wire.

DETAILED DESCRIPTION OF THE PREFERRED EMBODIMENTS

Figures 1, 3A, 3B:
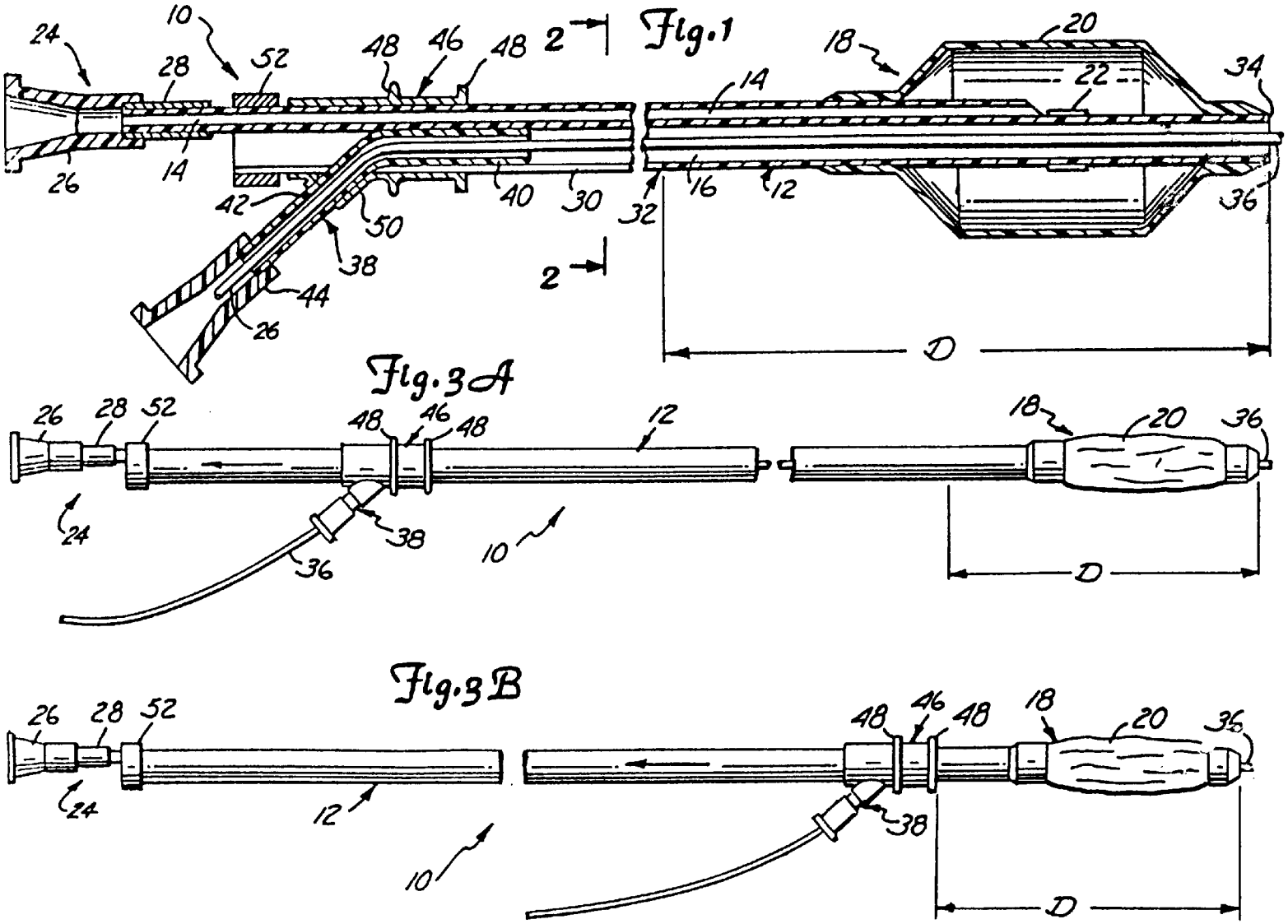
FIG. 1 is a sectional view of the peel-away dilatation balloon catheter of the present invention, with the balloon shown in an inflated condition.
FIGS. 3A and 3B show sectional views of the proximal end portion of the peel-away dilatation catheter of FIG. 1 illustrating movement of the catheter tube with respect to the stripper hub as the catheter is withdrawn from the patient while the guide wire stays in place.

Peel-away dilatation balloon catheter 10 of the present invention shown in FIG. 1 includes a dual lumen catheter tube 12 which has an inflation lumen 14 and a through lumen or insertion lumen 16. Mounted at distal end 18 of tube 12 is inflatable balloon 20. Inflation lumen 14 opens into the interior of balloon 20. Also shown within the interior of balloon 20 is a mid-balloon radiopaque marker 22, which is useful for identifying the location of balloon 20 by fluoroscopy.

In a preferred embodiment of the present invention, tube 12 is an extruded dual lumen tube made from polyethylene. Balloon 20 is formed from a polymer material such as polyolefin, and is bonded to tube 12 at the proximal and distal ends of balloon 20 by a suitable adhesive, such as an epoxy.

At proximal end 24 of catheter tube 12, inflation port 26 is connected through strain relief sleeve 28 to inflation lumen 14. Inflation port 26 is preferably a luer fitting which is attached to an inflation device (not shown).

Figure 2:
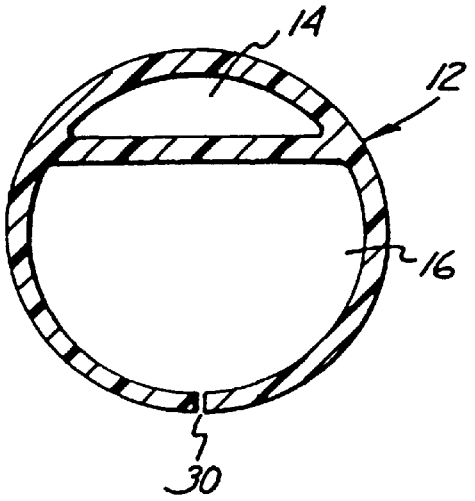
FIG. 2 is a sectional view along section 2—2 of FIG. 1 showing the dual lumen catheter tube of the peel-away catheter of FIG. 1.

As shown in FIGS. 1 and 2, tube 12 has a longitudinally extending opening or slit 30 which communicates with insertion lumen 16. Slit 30 extends from proximal end 24 of tube 12 to end point 32, which is located near the proximal portion of inflation balloon 20. The slit 30 is resiliently closed under normal conditions, however, it may be forcibly opened. In a preferred embodiment, the distance D between distal tip 34 of catheter 10 and end point 32 of slit 30 is approximately ten inches. This distance D is selected to be less than a normal length of catheter guide wire which extends outside beyond the proximal end of the catheter during an angioplasty procedure.

In FIG. 1, peel-away catheter 10 is shown in place on guide wire 36, which may be of any conventional design (including a "dilating guide wire" which has a small diameter balloon at its distal end). The distal end of guide wire 36 extends out through distal tip 34 of catheter 10. Guide wire 36 extends all the way through insertion lumen 16 and out insertion lumen hub 38 at the proximal end 24 of catheter 10. *As illustrated in FIG. 1, the guide wire 36 is laterally displaced from the proximal end 24 of the catheter 10.* Insertion lumen hub 38 includes a first tubular section 40 which is generally axially aligned with catheter tube 12 and is positioned within insertion lumen 16. Hub 38 also has a second tubular portion 42 which extends at an angle outward through slit 30. The outer end of tubular section 42 carries a luer fitting 44. Insertion lumen hub 38 is carried by and is movable with stripper hub 46.

Stripper hub 46 is a generally cylindrical sleeve having a pair of ribs 48 for gripping and having a side port 50 through which tube section 42 of insertion lumen hub 38 extends. Stripper hub 46 is slidable in an axial direction along the length of catheter tube 12 between the position shown in FIG. 1 and a position which is limited by the end point 32 of slit 30. Stop collar 52 is attached to the proximal end of catheter tube 12 to stop the proximal motion of stripper hub 46 and prevent it from being removed off the proximal end of catheter tube 12.

Catheter 10 of the present invention has the advantage of being able to be removed from the patient while leaving guide wire 36 in place. FIGS. 3A and 3B, together with FIG. 1, illustrate the "peel-away" removal of catheter 10 over guide wire 36. *As illustrated in FIGS. 3A and 3B, the guide wire 36 is laterally displaced from the catheter tube 12.*

In FIG. 3A, the withdrawal of catheter 10 from the patient has begun. By comparing FIG. 3A with FIG. 1, it can be seen that stripper hub 46 is no longer adjacent proximal end 24 of tube 12. This is accomplished by the physician by holding stripper hub 46 in place, while applying force to the proximal end of cathether 10 so that relative movement of catheter tube 12 with respect to stripper hub 46 is taking place. FIG. 3B shows catheter 10 at a position where end point 32 has reached stripper hub 46. At this point distal tip 34 is either outside of the guide catheter (not shown) or can be pulled outside the guide catheter by proximal movement of catheter 10, so that it is possible for the physician to grasp a portion of guide wire 36 distally of tip 34. The remaining distance D of catheter 10 can be pulled off of the guide wire 36 without disturbing guide wire 36, because it is possible to grasp guide wire 36 at a position between distal tip 34 and the guide catheter.

Once catheter 10 has been removed from guide wire 36, a different dilatation catheter of either the same, or different construction can be threaded over guide 36 and into the patient. Through the entire procedure, the distal end of guide wire 36 has remained in place within the patient. This is advantageous because it avoids the time required to reinsert the guide wire; it avoids the cost of an exchange wire and the handling problems associated with an exchange wire; and it reduces the danger involved in recrossing a freshly crossed lesion.

Figure 4A:
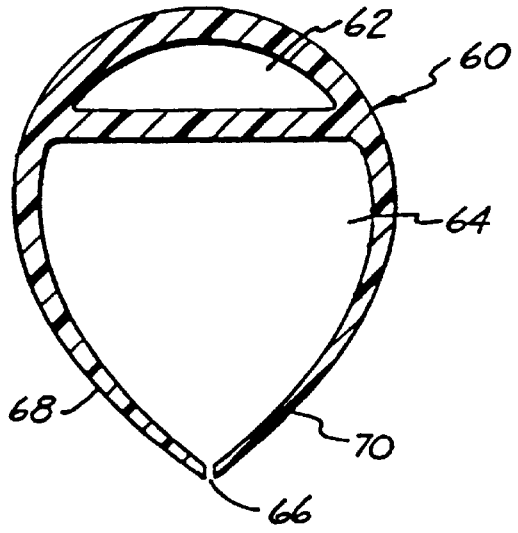
FIGS. 4A and 4B are sectional views illustrating a method of forming an alternate construction of the dual lumen catheter tube.
Figure 4B:
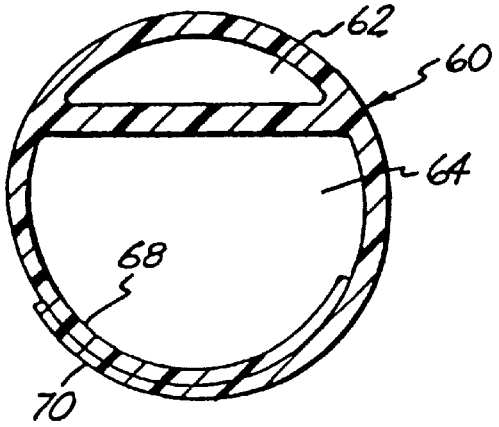

FIGS. 4A and 4B illustrate an alternative embodiment of the present invention. As shown in FIG. 4A, catheter tube 60 is a dual lumen tube having an inflation lumen 62 and a through lumen or insertion lumen 64. Slit 66 extends through the wall of tube 60 in an area of reduced wall thickness to divide the outer wall of tube 60 into two flaps 68 and 70.

As shown in FIG. 4B, tube 60 is then compressed or heat formed so that flap 70 overlaps flap 68 (or vice versa). This overlapping provides greater structural strength for tube 60, while still allowing flaps 68 and 70 to be parted as there is relative movement between stripper hub 46 and tube 60.

FIGS. 5A and 5B, 6A and 6B, 7A and 7B, and 8A and 8B illustrate other embodiments which feature extruded dual lumen tubing with resealable slits. The advantages of a resealable slit are that no blood leakage occurs, and that the through lumen can also be used for blood pressure measurement and distal dye delivery.

Figure 5A:
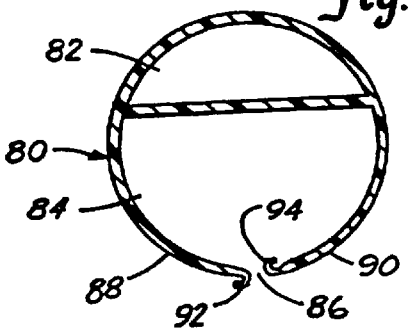
FIGS. 5A and 5B, 6A and 6B, 7A and 7B and 8A and 8B are sectional views illustrating other embodiments of the dual lumen catheter tube with resealable slits.
Figure 5B:
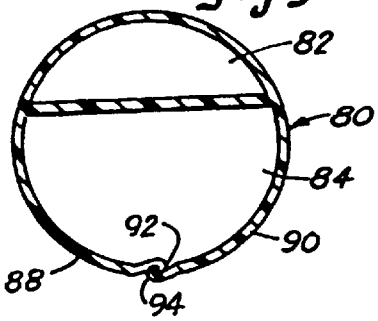

In FIGS. 5A and 5B, catheter tube 80 is a dual lumen tube having an inflation lumen 82 and a through lumen 84. Slit 86 (which is open in FIG. 5A and closed in FIG. 5B) divides the outer wall of tube 80 into flaps 88 and 90. C-shaped hooks 92 and 94 at the edges flaps 88 and 90 respectively, run longitudinally the length of slit 86, and engage one another to seal slit 86 as shown in FIG. 5B. The seal provided by hooks 92 and 94 can be broken to open slit 86 by relative movement of stripper hub 46.

Figure 6A:
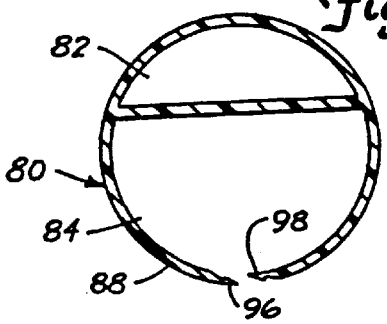
Figure 6B:
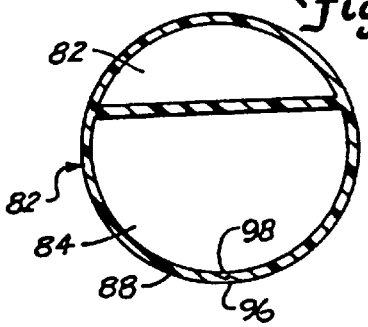
Figure 7A:
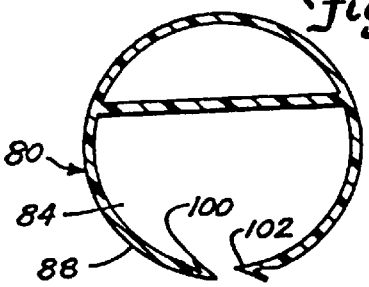
Figure 7B:
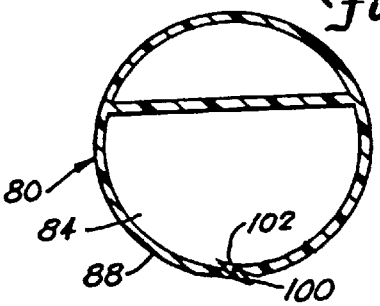
Figure 8A:
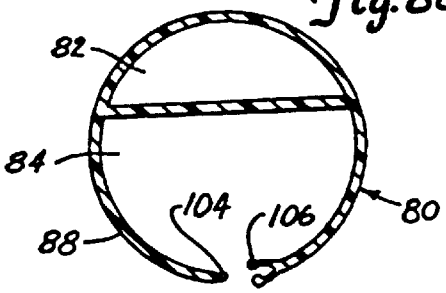
Figure 8B:
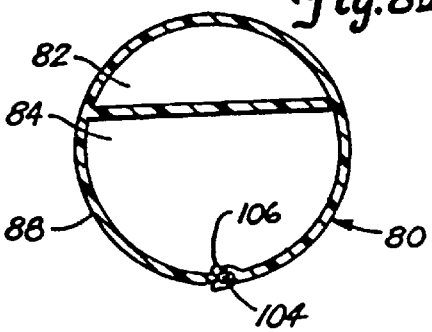

The embodiments shown in FIGS. 6A and 6B, 7A and 7B, and 8A and 8B are generally similar to FIGS. 5A and 5B (and similar reference numerals are used). In FIGS. 6A and 6B, ramp hooks 96 and 98 replace C-shaped hooks 92 and 94. In FIGS. 7A and 7B, barbs 100 and 102 replace hooks 92 and 94. In FIGS. 8A and 8B, ball 104 and socket 106 replace hooks 92 and 94.

Figure 9:
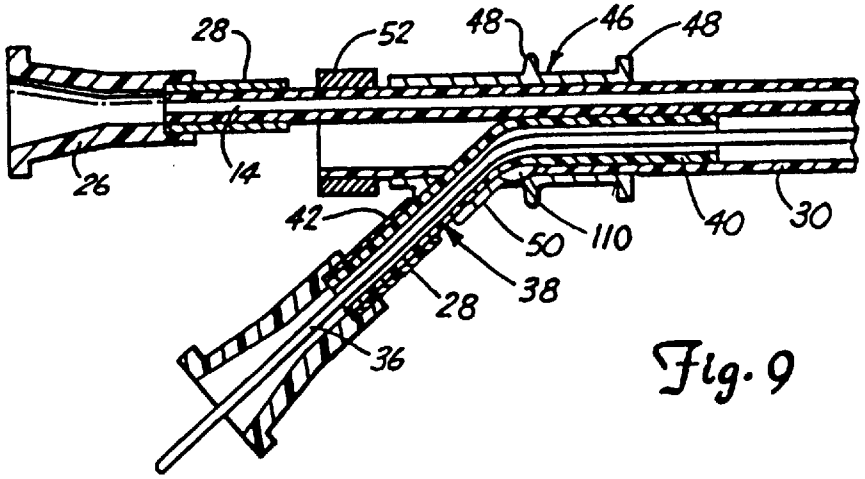
FIG. 9 is a sectional view of the proximal end of another embodiment of the peel-away catheter of the present invention.

FIG. 9 shows the distal portion of another embodiment of the peel-away catheter which is generally similar to the embodiment of FIGS. 1–3, and similar reference characters are used. The embodiment of FIG. 9 include knife blade 110 which is carried by stripper hub 46. Relative movement of stripper hub 46 toward the distal end of catheter 10 cause knife blade 110 to cut a slit in tubing 12 (which was extruded without a slit). The advantage of this embodiment is that until the time of slitting no blood leakage can occur and blood pressure measurements and distal dye delivery can be accomplished by using through lumen 16.

Figure 10:
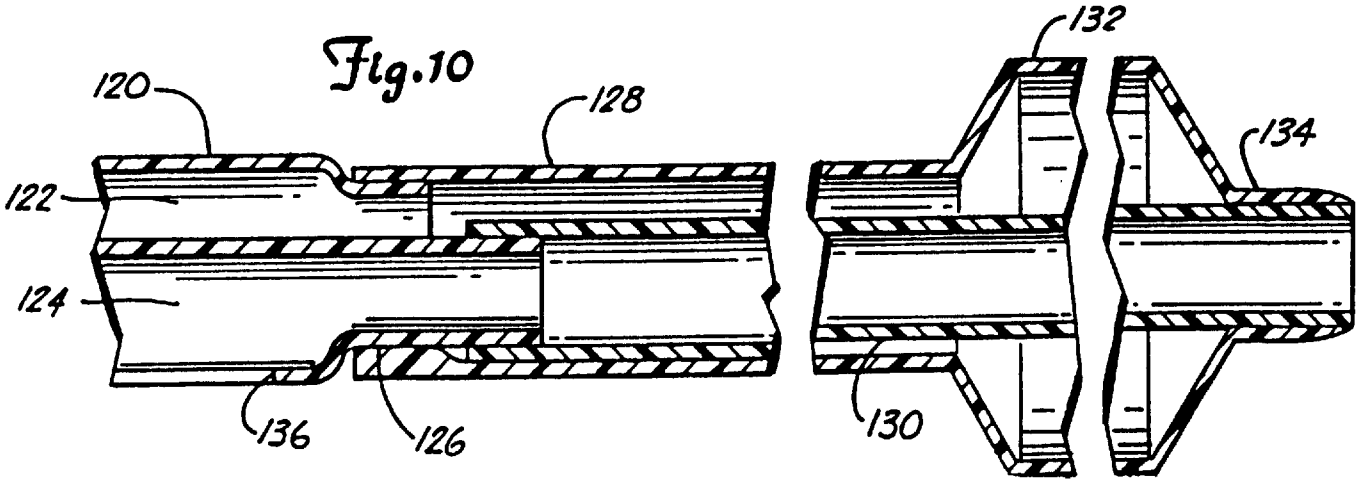
FIG. 10 is a sectional view of the distal end of still another embodiment of the peel-away catheter.

FIG. 10 shows the distal portion of still another embodiment of the peel-away catheter. In this embodiment, dual lumen tubing 120 can take any one of several forms, including the forms shown and discussed previously. Tubing 120 has an inflation lumen 122 and a through lumen 124. At its distal end, tubing 120 has a reduced diameter bonding region 126 to which balloon waist 128 is bonded. Through lumen 124 extends distally slightly beyond inflation lumen 122 and has an extension inner lumen 130 connected at its distal end. Connected to balloon waist 128 is inflatable balloon segment 132 (shown inflated). Balloon waist 128, inflatable balloon segment 132 and distal bond segment 134 may be a one-piece (integral) construction or may be formed of different materials. Distal bond segment 134 is bonded to the distal end of inner lumen 130.

In FIG. 10, the longitudinal slit in tubing 120 extends to point 136, which is near bonding region 126. The distance from point 136 to the distal tip of the catheter is approximately ten inches.

In conclusion, the peel-away catheter of the present invention provides a simple yet very effective way of performing an angioplasty dilatation catheter exchange without having to remove the guide wire from the patient. With the present invention, it is not necessary to provide a guide wire of excessive length for those occasions where a catheter exchange is required, and yet the physician can make an exchange quickly and simply in those cases where it becomes apparent that catheter exchange is necessary.

Another important advantage of the present invention is that it provides maximum pushability through the patient because the guide wire 36 supports catheter 10 along its entire length.

During insertion of a catheter 10 of this design, the tripper hub 46 may be located at the proximal end 24 of slit 30 and insertion made by a traditional threading onto guide wire 36.

Alternatively, stripper hub 46 and insertion hub 38 may be located near the patient. In this arrangement, the catheter tubing 12 is pushed through the stripper hub 46, resiliently closes over the guide wire 36 and enters the patient.

Although the present invention has been described with reference to preferred embodiments, workers skilled in the art will recognize that changes may be made in form and detail without departing from the spirit and scope of the invention.

What is claimed is:

1. A catheter which is insertable and removable over a guide wire which has one end adapted for insertion into a vessel of a patient and an opposite end which extends outside of the patient, the catheter comprising:

a tubular member having a proximal end, a distal end, a first lumen for transmitting fluid, and a second lumen through which the guide wire passes;

an inflatable balloon carried by the tubular member adjacent the distal end and in communication with the first lumen;

wherein the tubular member includes a longitudinal opening through a side wall of the tubular member and connected to the second lumen, the longitudinal opening extending from adjacent the proximal end of the tubular member to a position spaced from a proximal end of the inflatable balloon and dividing the side wall into first and second wall portions on opposite sides of the longitudinal opening, with the longitudinal opening permitting movement of the guide wire through the longitudinal opening as the tubular member is removed from the patient while the guide wire remains in the patient; interlocking means carried adjacent longitudinal free edge portions of the first and second wall portions, and including first interlocking means carried at a longitudinal free edge of the first wall portion and second interlocking means carried at a longitudinal free edge of the second wall portion, the first and second interlocking means being selectively interlockable to close the longitudinal opening; and a generally cylindrical sleeve member slidably mounted about the tubular member, the sleeve member having a tubular section through which the guide wire extends and which disengages the interlocking means and locally spreads apart the longitudinal opening to permit passage of the tubular section and guide wire therethrough.

2. The catheter of claim 1 wherein the interlocking means includes a pair of cooperable resilient flaps which resiliently closes the longitudinal opening to prevent passage of the guide wire therethrough with a first flap extending along the longitudinal free edge portion of the first wall portion and overlapping a second flap extending along the longitudinal free edge portion of the second wall portion.

3. The catheter of claim 2 wherein the flaps have thinner wall sections adjacent the longitudinal opening and thicker wall sections away from the opening.

4. The catheter of claim 1 wherein the tubular section of the sleeve member includes an insertion hub having:

a first tubular portion generally axially aligned with the tubular member and positioned within the second lumen;

a second tubular portion extending at an angle from the first tubular section outward through the longitudinal opening; and wherein the guide wire passes through the first and second portions of the insertion hub.

5. The catheter of claim 4 wherein the second tubular portion of the insertion hub includes a luer fitting through which the guide wire passes.

6. The catheter of claim 4 wherein the sleeve member includes:

a side port therethrough for the second tubular portion; and wherein the sleeve member is slidable on the tubular member of the catheter over a span of the longitudinal opening.

7. The catheter of claim 1 wherein the sleeve member includes at least one exterior rib which extends circumferentially about the sleeve member for facilitating gripping of the sleeve member.

8. The catheter of claim 1 wherein the tubular member includes a stop collar adjacent the proximal end for limiting the motion of the sleeve member in a proximal direction.

9. The catheter of claim 1 wherein a distance from the position spaced from the proximal end of the inflatable balloon to the distal tip of the catheter is approximately ten inches.

10. The catheter of claim 1 wherein the first and second interlocking means further comprise:

a first C-shaped hook and a second C-shaped hook, the first C-shaped hook extending along the longitudinal free edge of the first wall portion and being cooperable with the second C-shaped hook extending along the longitudinal free edge of the second wall portion.

11. The catheter of claim 1 wherein the first and second interlocking means further comprise:

a first ramp-shaped hook and a second ramp-shaped hook, the first hook extending along the longitudinal free edge of the first wall portion and being cooperable with the second hook extending along the longitudinal free edge of the second wall portion.

12. The catheter of claim 1 wherein the first and second interlocking means further comprise:

a first barb-shaped hook and a second barb-shaped hook, the first hook extending along the longitudinal free edge of the first wall portion and being cooperable with the second hook extending along the longitudinal free edge of the second wall portion.

13. The catheter of claim 1 wherein the first and second interlocking means further comprise:

a rib portion and a groove portion, the rib portion extending along the longitudinal free edge of the first wall portion and being cooperable with the groove portion extending along the longitudinal free edge of the second wall portion.

14. A method of removing a balloon catheter from a patient while leaving a guide wire in place with a proximal end of the guide wire outside the patient and a distal end of the guide wire within the patient, the method comprising:

providing a generally cylindrical stripper hub about a proximal end of the balloon catheter which extends outside of the patient;

applying force to the balloon catheter at its proximal end in a direction which causes the balloon catheter to be withdrawn proximally through the stripper hub and out of the patient;

maintaining the guide wire in an essentially stationary position, by grasping the stripper hub and maintaining the stripper hub in an essentially stationary position relative to the patient to cause a longitudinal slit in a side wall of the balloon catheter to open by separating interlocked interlocking means carried on opposing wall portions of the side wall defining the slit, as the balloon catheter passes proximally through the stationary stripper hub and to permit the guide wire to pass generally laterally out through the longitudinal slit in the side wall of the balloon catheter until a remaining length of the catheter positioned over the guide wire is shorter than a length of the guide wire extending outside the patient; and removing the remaining length of balloon catheter proximally off of the guide wire.

15. The method of claim 14 wherein the applying force step and the maintaining the guide wire position step are performed simultaneously.

16. The method of claim 14 and further comprising:

grasping a portion of the guide wire located distally of a distal tip of the balloon catheter when that portion of the balloon catheter becomes exposed outside of the patient.

17. The method of claim 16 wherein the grasping step and the removing step are performed essentially simultaneously.

18. A method of exchanging a first angioplasty dilation catheter in a patient with a second angioplasty dilation catheter while leaving a guide wire in place with a proximal end of the guide wire outside the patient and a distal end of the guide wire within the patient, the method comprising:

providing a generally cylindrical stripper hub about a proximal end of the first angioplasty dilation catheter which extends outside of the patient;

applying force to the first catheter at its proximal end in a direction which causes the first catheter to be withdrawn proximally through the stripper hub and out of the patient;

maintaining the guide wire in an essentially stationary position, by grasping the stripper hub and maintaining the stripper hub in an essentially stationary position relative to the patient to cause a longitudinal slit in a side wall of the first catheter to open by separating interlocked interlocking means carried on opposing wall portions of the side wall defining the slit as the first balloon catheter passes proximally through the stationary stripper hub and to permit the guide wire to pass laterally out through the longitudinal slit in the side wall of the first catheter and through a side port in the stripper hub until a remaining length of the first catheter positioned over the guide wire is shorter than length of the guide wire extending outside the patient;

removing a remaining length of the first catheter proximally off of the guide wire;

threading the second angioplasty dilation catheter onto the proximal end of the guide wire; and inserting the second angioplasty dilation catheter into the patient and over the guide wire within the patient.

19. A catheter which is insertable and removable over a guide wire, the catheter comprising:

an inflatable balloon;

a shaft supporting the balloon at a distal end thereof, and having an inflation port at a proximal end thereof, the shaft having an inflation lumen extending from the inflation port to an interior of the balloon and a guide wire lumen extending through the interior of the balloon, with the guide wire lumen comprising means for releasably holding a guide wire adjacent to the inflation lumen along substantially an entire length of the shaft and said guide wire lumen including interlocking parting means for permitting the shaft and the guide wire to be peeled away from one another along substantially the entire length of the shaft; and a generally cylindrical sleeve member mounted about the shaft which is capable of relative longitudinal movement with respect to the shaft for causing the parting means to unlock and be parted, thereby permitting the shaft and guide wire to be peeled apart.

*20. A balloon catheter, comprising:*

*a. an elongate shaft having a proximal end, a distal end, an exterior and a guide wire lumen extending therethrough, the distal end of the shaft including an inner tube disposed in an outer tube, the elongate shaft also having a longitudinal slit extending distally from the proximal end of the shaft to provide access to the guidewire lumen from the exterior of the shaft, wherein the slit is defined between adjacent flaps when the slit is open, and wherein the flaps provide structural strength to the shaft when the slit is closed;*

*b. an inflatable balloon having a proximal end and a distal end, the proximal end of the balloon connected to the distal end of the shaft;*

*c. a guide wire having a proximal end and a distal end, the distal end being disposed in the guide wire lumen and the proximal end being laterally displaced from the elongate shaft; and*

*d. a sliding member disposed on the elongate shaft and extending at least partially into the longitudinal slit, the sliding member engaging the guide wire disposed in the guide wire lumen.*

*21. A balloon catheter as in claim 20, wherein a distal end of the inner tube is connected to the distal end of the balloon and a distal end of the outer tube is connected to the proximal end of the balloon.*

*22. A balloon catheter as in claim 21, wherein the inner tube is about 10 inches long.*

*23. A balloon catheter, comprising:*

*a. a proximal shaft having a proximal end, a distal end, an exterior and a proximal guide wire lumen extending therethrough, the proximal shaft also having a longitudinal slit to provide access to the proximal guide wire lumen from the exterior of the shaft, wherein the slit is defined between adjacent flaps when the slit is open and wherein the flaps provide structural strength to the proximal shaft when the slit is closed;*

*b. an outer tube having a proximal end and a distal end, the proximal end of the outer tube connected to the distal end of the proximal shaft;*

*c. an inner tube having a proximal end, a distal end and a distal guide wire lumen extending therethrough, the inner tube disposed in the outer tube to define an annular lumen therebetween; and*

*d. a balloon having a proximal end and a distal end, the proximal end of the balloon connected to the distal end of the outer tube, the distal end of the balloon connected to the distal end of the inner tube.*

*24. A balloon catheter as in claim 23, further comprising:*

*e. a sliding member disposed on the proximal shaft and extending at least partially into the longitudinal slit.*

*25. A balloon catheter as in claim 24, further including a guide wire disposed in the proximal guide wire lumen, wherein the sliding member engages the guide wire.*

*26. A balloon catheter as in claim 25, wherein the inner tube is about 10 inches long.*

*27. A balloon catheter, comprising:*

*a. a first shaft having a proximal end, a distal end, a first inflation lumen extending therethrough, and a first guide wire lumen extending therethrough, the first shaft also having a slit extending therealong to provide access to the first guide wire lumen, wherein the slit is defined between adjacent flaps when the slit is open, and wherein the flaps provide structural strength to the first shaft when the slit is closed;*

*b. a second shaft having a proximal end, a distal end, a second inflation lumen extending therethrough, and a second guide wire lumen extending therethrough, the proximal end of the second shaft connected to the distal end of the first shaft, the second shaft having a length of about 10 inches; and*

*c. a balloon connected to the distal end of the second shaft.*

*28. A balloon catheter as in claim 27, wherein the slit terminates at the distal end of the first shaft.*

*29. A balloon catheter as in claim 27, further comprising:*

*d. a sliding member disposed in the slit.*

*30. A balloon catheter as in claim 29, further including a guide wire disposed in the proximal guide wire lumen, wherein the sliding member engages the guide wire.*

*31. A balloon catheter as in claim 30, wherein the slit terminates at the distal end of the first shaft.*

*32. A balloon catheter, comprising:*

*a. an elongate shaft having a proximal end, a distal end, an exterior, a guide wire lumen, an inflation lumen, and a longitudinally-extending lateral opening which provides access to the guide wire lumen from the exterior of the shaft, wherein the lateral opening is defined between adjacent flaps when the lateral opening is open, and wherein the flaps provide structural strength to the shaft when the lateral opening is closed;*

*b. an inflatable balloon connected to the distal end of the elongate shaft, the inflatable balloon being in fluid communication with the inflation lumen;*

*c. a guide wire disposed in the guide wire lumen; and*

*d. a sleeve member slidably disposed on the shaft, the sleeve member including a portion which penetrates the lateral opening into the guide wire lumen and at least partially surrounds the guide wire disposed in the guide wire lumen, the portion of the shaft proximal of the sleeve member remaining substantially coaxially aligned with the portion of the shaft distal of the sleeve member.*

*33. A balloon catheter as in claim 32, wherein the longitudinally extending lateral opening extends to a point about 10 inches proximal of the balloon.*

*34. A balloon catheter as in claim 32, wherein the distal end of the elongate shaft includes an inner tube disposed in an outer tube.*

*35. A balloon catheter as in claim 34, wherein a distal end of the inner tube is connected to a distal end of the balloon and a distal end of the outer tube is connected to a proximal end of the balloon.*

*36. A balloon catheter as in claim 35, wherein the inner tube is about 10 inches long.*

* * * * *